(12) United States Patent
Zanghi

(10) Patent No.: US 8,492,331 B2
(45) Date of Patent: Jul. 23, 2013

(54) METHODS FOR INCREASING ABSORPTION OF PEPTIDES, PEPTIDOMIMETICS AND OTHER GASTROINTESTINAL TRANSPORT PROTEIN SUBSTRATES

(75) Inventor: Brian Michael Zanghi, Gowanda, NY (US)

(73) Assignee: Nestec S.A., Vevey (CH)

( * ) Notice: Subject to any disclaimer, the term of this patent is extended or adjusted under 35 U.S.C. 154(b) by 267 days.

(21) Appl. No.: 12/736,248

(22) PCT Filed: Mar. 26, 2009

(86) PCT No.: PCT/US2009/001937
§ 371 (c)(1),
(2), (4) Date: Sep. 23, 2010

(87) PCT Pub. No.: WO2009/120378
PCT Pub. Date: Oct. 1, 2009

(65) Prior Publication Data
US 2011/0015117 A1    Jan. 20, 2011

Related U.S. Application Data

(60) Provisional application No. 61/072,069, filed on Mar. 27, 2008.

(51) Int. Cl.
*A61K 31/4045* (2006.01)

(52) U.S. Cl.
USPC .......................................................... 514/1.2

(58) Field of Classification Search
None
See application file for complete search history.

(56) References Cited

U.S. PATENT DOCUMENTS 5,508,039 A * 4/1996 Yates et al. .................... 424/448
2004/0009922 A1 * 1/2004 Mochly-Rosen ............... 514/16

OTHER PUBLICATIONS

Tekbas OF, Ogur R, Korkmaz A, Kilic A, Reiter RJ, "Melatonin as an antibiotic: new insights into the actions of this ubiquitous molecule," J. Pineal Res., Mar. 1, 2008, 44: 222-226.*
Qi et al, "Melatonin Reduces Lipid Peroxidation and Tissue Edema in Cerulein-Induced Acute Pancreatitis in Rats," Nov. 1999, 44(11): 2257-2262.*
Skaper et al, "Excitotixicty, Oxidative Stress, and the Neuroprotective Potential of Melatonin," Annals New York Academy of Sciences, 2006, 107-118.*
Gaildrat et al, "A Novel Pineal-specific Product of the Oligopeptide Transporter PepT1 Gene," JBC, 2005, 280(17): 16851-16860.*

* cited by examiner

*Primary Examiner* — Julie Ha
(74) *Attorney, Agent, or Firm* — Julie M. Lappin; Janet E. Reed

(57) ABSTRACT

Methods and compositions useful for enhancing the absorption and/or transport of peptides, peptidomimetics, and other gastrointestinal transport protein substrates through gastrointestinal transport proteins are provided. The methods comprise using hormones such as 5-methoxy-N-acetyl-tryptamine to increase the transport of the peptides, peptidomimetics, and substrates. The compositions comprise one or more hormones and one or more peptides, peptidomimetics, and other gastrointestinal transport protein substrates.

11 Claims, No Drawings

METHODS FOR INCREASING ABSORPTION OF PEPTIDES, PEPTIDOMIMETICS AND OTHER GASTROINTESTINAL TRANSPORT PROTEIN SUBSTRATES

CROSS REFERENCE TO RELATED APPLICATIONS

This application is a national stage application under 35 U.S.C. §371 of PCT/US2009/001937 filed Mar. 26, 2009, which claims priority to U.S. Provisional Application Ser. No. 61/072,069 filed Mar. 27, 2008, the disclosures of which are incorporated herein by reference.

BACKGROUND OF THE INVENTION

1. Field of the Invention

The invention relates generally to methods for increasing absorption of compounds by an animal and particularly to the use of hormones such as 5-methoxy-N-acetyltryptamine to increase absorption of peptides, peptidomimetics, and other gastrointestinal transport protein substrates by an animal.

2. Description of the Related Art

Peptide transporter proteins are integral membrane proteins that mediate the cellular uptake of di- and tripeptides and a variety of peptidomimetics and other compounds. They are found in bacteria, yeast, plants, invertebrates, and vertebrates. In vertebrates, two transporter proteins, Peptide transporter 1 and 2, designated PepT1 and PepT2 respectively, are expressed predominantly in brush border membranes of small intestine (PepT1), kidney (PepT1 and PepT2), and lung (PepT2). The PepT transporters are proton-coupled transporters capable of transporting numerous dipeptides and tripeptides, as well as a large spectrum of therapeutic drugs like β-lactam antibiotics, selected angiotensin-converting enzyme (ACE) inhibitors, and peptidase inhibitors. It is believed that substrate flux is coupled to proton movement down an electrochemical proton gradient with the membrane potential as the main driving force for the translocation.

Mammalian oligopeptide transporters are part of the PTR2 family of membrane transporters. They are characterized by two signature motifs that are conserved in all known family members. The first conserved motif is a region that begins at the end of the second putative transmembrane domain, including the following first cytoplasmic loop as well as the third transmembrane domain. The second conserved motif corresponds to the core region of the fifth transmembrane region. Besides the mammalian PepT1 and PepT2 transporter proteins, the PTR2 family includes the yeast peptide transporter PTR2, DtpT from *Lactococcus lactis*, and numerous "orphan" transporters having unknown functions. Most orphan transporters are found in prokaryotes such as *Escherichia coli*.

In mammals, PepT1 plays an important role in the absorption of proteins, including small oligopeptides. PepT1 is expressed primarily in the brush-border membranes of intestinal epithelial cells where it mediates the transport of oligopeptides, such as those found in digests, from the gut lumen into the cells. In addition, because of its relatively broad substrate specificity, PepT1 can accept various pharmacologically-active compounds, including β-lactam antibiotics, and serve as an absorptive pathway for these compounds. Functional studies have shown that, in addition to utilizing the H+ electrochemical gradient as a driving force, PepT1 exhibits pH-dependence, and is reported to be a high-velocity, low-affinity transporter. PepT1 is also reportedly an inducible transporter. Inducers include substrates, substrate analogs, and various hormones.

Physiological stresses, including intestinal illness, physical stress, surgery, injury, and/or mental stress can negatively influence intestinal health and function, directly or indirectly affecting amino acid absorption. For example, it has been shown that rats with Type 1 diabetes (i.e., naturally low or absent insulin production) had a reduced PepT1 activity compared to healthy rats.

Attempts have been made to improve amino acid absorption. For example pre-digesting dietary protein and adding the hydrolyzed dietary protein to foods, such as critical care foods has been used, however, such approaches primarily increase the pool of amino acids or peptides available for absorption, and do not necessarily enhance the absorption process. Some specific small peptides can apparently stimulate peptide absorption. Methods of feeding specific peptides, particularly glycylsarcosine or β-alanyl-L-histidine (carnosine), to increase peptide absorption in a canine cell line were disclosed in U.S. Pat. No. 6,803,186, but in vivo, the use of these peptides was not successful in stimulating peptide absorption compared to the standard diet alone. It has been indicated that a dipeptide, alanyl-glutamine, alone was not sufficient to stimulate peptide absorption activity; however, when combined with growth hormone (GH), peptide absorption was maintained when a human cell line was subjected to oxidative stress by hydrogen peroxide. Peroxide-induced oxidative stress reduced peptide absorption in the absence of peptide and GH. Some scientific literature indicates that certain active biological peptides or hormones can stimulate small peptide absorption, through directly stimulating the activity of PepT1. Insulin, epidermal growth factor, leptin, interferon-gamma, and thyroid hormone have all shown some stimulating effect. Conflicting data has been reported regarding any stimulatory effect of growth hormone.

With the exception of thyroid hormone, the stimulatory peptide hormones are species-specific proteins. Thus, application or use of these in practice would require, for example, synthesis by chemical or recombinant gene techniques for each species in which the hormones were to be used. Further, it appears that these hormones have been administered by subcutaneous injection, which is not desirable in actual application.

Other efforts have been made to specifically regulate the transport activity of PepT1 for various purposes. For example, U.S. Patent Application US20030170748A1 discloses nucleic acids encoding a canine PepT1. The publication also evaluated the absorption of certain peptide-bound forms of leucine and tryptophan, as well as the ability of various small peptides to inhibit the transport of a model substrate, glycylsarcosine (GlySar). Methods are provided for determining whether a particular peptide is likely to have a beneficial nutritional property to an animal, and for stimulating PepT1 activity in cells by contacting the cells with a PepT1 substrate. Similarly, U.S. Patent Application US20060210569A1 discloses methods of inhibiting PepT1, thereby inhibiting cell-growth.

There remains a need, therefore, for methods of increasing absorption or uptake in an animal of one or more specified or unspecified peptides, peptidomimetics and other gastrointestinal transport protein substrates, particularly through transporter proteins such as the PepT1 transporter.

SUMMARY OF THE INVENTION

It is, therefore, an object of the present invention to provide methods for enhancing, improving, or increasing the absorption, transport, uptake, and/or assimilation of peptides, peptidomimetics, or other gastrointestinal transport protein substrates in an animal.

It is a further object of the invention to provide beneficial methods for supporting and/or improving gastrointestinal health, promoting the health or wellness of an animal, providing improved amino acid nutrition to animals with malabsorptive disorders, delivering drugs or prodrugs that are substrates for a gastrointestinal transport protein, and maintaining muscle mass in an aging animal or an animal subjected to strenuous physical activity, e.g., exercise.

One or more of these and other objects are achieved using novel compositions and methods useful enhancing transport of peptides, peptidomimetics, or other gastrointestinal transport protein substrates in an animal. The methods comprise administering an amount of one or more melatonins effective for enhancing transport of peptides, peptidomimetics, or other gastrointestinal transport protein substrates through an intestinal transport protein in the animal, e.g., PepT1. The methods improve the absorption of these compounds and increase the amounts of such compounds available for the animal to use for their intended purpose, e.g., build protein or combat infections. The methods also enhance the nutritive value of a food composition in vivo when the food composition is administered to an animal in conjunction with an amount of melatonin sufficient for enhancing absorption of one or more di-or tripeptides in the composition or its natural digestion products. The compositions comprise melatonin and one or more peptides, peptidomimetics, or other gastrointestinal transport protein substrates.

Other and further objects, features, and advantages of the present invention will be readily apparent to those skilled in the art.

DETAILED DESCRIPTION OF THE INVENTION

Definitions

The term "melatonin" means 5-methoxy-N-acetyltryptamine and its derivatives or analogs that have substantially the same biological activity as 5-methoxy-N-acetyltryptamine, and their in vivo precursors. 5-methoxy-N-acetyltryptamine is a compound that varies in amount during the diurnal cycle. The compound is produced by the pineal gland, the retina, immune cells, and the gastrointestinal tract. It is naturally synthesized from the amino acid tryptophan via synthesis of serotonin. The pineal gland receives information from the retina about the daily pattern of light and darkness and synthesizes melatonin in response. The compound is also synthesized by various plants such as rice and by bacteria, protozoa, algae, and other organisms. The term also means any other hormone that has substantially the same biological activity as 5-methoxy-N-acetyltryptamine on gastrointestinal transport proteins such as PepT1 and PepT2.

The term "peptidomimetic" means a compound that mimics one or more structural aspects or biological activities of a naturally-occurring oligopeptide, but which comprises one or more non-peptide or non-naturally occurring chemical structures or bonds. The peptidomimetics for use herein have one or more biological properties related to oligopeptide transport in an animal. In one presently preferred embodiment, a peptidomimetic as used herein is recognized by one or more oligopeptide transport proteins, for example as a substrate, inhibitor, agonist or antagonist. In another embodiment, a peptidomimetic is an inducer of one or more oligopeptide transport proteins; i.e., the peptidomimetic induces the amount or activity of the oligopeptide transport protein without being directly recognized as a substrate or agonist of the protein. Peptidomimetics are frequently used to mimic the biological action of a peptide, thus they may be small protein-like chain designed to mimic one or more peptides. Peptidomimetics are often synthesized based on existing peptides of interest with one or more modifications to alter the molecule's structure or properties. Modifications can change the peptide molecule's stability, half-life, biological activity, absorption, or side-effects (e.g., toxicity, solubility, hydrophobicity, side-chain charge or flexibility,) of a peptide. Peptidomimetics can be useful as medicaments or drug-like compounds developed rationally, or based on modification of an existing peptide with known or putative biological activity. Peptidomimetics as used herein preferably comprise one or modifications that do not occur naturally, e.g., modified or altered peptide backbone structure, the incorporation of non-natural amino acids, and the like.

In several embodiments, the peptidomimetics for use herein are medicaments. It is known in the art of drug delivery that certain drugs or classes of drugs can be delivered via protein or peptide transport molecules. For example, certain antibiotics, blood pressure regulating drugs (e.g., antihypertensives), antiviral medicaments and other drugs are substrates for or may be transported in vivo by one or more PTR2 family peptide transport molecules. For examples, peptidomimetic antibiotics, such as the β-lactam antibiotics can be transported in vivo by oligopeptide transporters. The β-lactam antibiotics are a broad class of antibiotics that contain a β-lactam ring in their molecular structure. The class includes penicillins cephalosporins, monobactams, carbapenems, including their derivatives. It should be noted, for purposes herein, discussion of compounds such as "peptidomimetics" includes all commonly-accepted forms and commercially-useful preparations of such compounds, such as salts, acids, bases, especially pharmaceutically-acceptable salts of such compounds. Other peptidomimetic compounds comprising β-lactam ring structures include β-lactamase inhibitors, which may not be antibacterial or antibiotic inherently, but which inhibit β-lactamase enzymes produced by microorganisms to degrade β-lactam-containing compounds in the environment. β-lactam antibiotics tend to be broad spectrum and are the most widely-used class of antibiotics. Cephalexin is one example of a cephalosporin antibiotic exemplified herein.

Peptidomimetics as used herein also encompass modifications, such as via amino acid esterification, of a variety of drugs or prodrugs. These modified drugs, e.g., amino acid esters, are useful herein because they can render the associated drug or prodrug transportable as a substrate, or an inducer, of an intestinal oligopeptide transport protein. This strategy is particularly useful where the drug is poorly absorbed otherwise. For example, the prodrug, midodrine, an antihypertensive, is converted to DMAE, its active form, in vivo, by cleavage of a glycyl residue. Midodrine, but not DMAE, is a substrate for PepT1 transport. Other amino acid modifications to DMAE also have the ability to be transported by PepT1. Examples of other drugs known to be substrates for intestinal oligopeptide transporters include valacyclovir and valganciclovir, which are amino acid ester prodrugs of the antivirals, acyclovir and ganciclovir respectively.

The skilled artisan will appreciate that determining whether a particular compound is a peptidomimetic within the meaning of the foregoing definition can be assessed by art-recognized methods. For example, a peptidomimetic compound may be an effective inhibitor, such as a competitive inhibitor, of the transport of one or more known substrates of an oligopeptide transporter. One such substrate for PepT1 is the model substrate, glycylsarcosine. The transport, binding, or absorption of a putative peptidomimetic can also be assessed directly in in vitro model systems, membranes, vesicles, cells, or in vivo animal systems. Other functional assays can be based on the fact the certain preferred intestinal oligopeptide transport proteins are proton-dependent transporters. Thus, assay of a putative peptidomimetic substrate can be based, for example, on proton movement, depolarization of membranes in which the intestinal oligopeptide transport protein is situated.

The terms "enhance" "enhances" and "enhancing" used herein with respect to absorption, transport, uptake, or assimilation of peptides, peptidomimetics, other gastrointestinal transport protein substrates, or other compounds means that a particular composition or method has some measurable effect on such absorption, transport, uptake, or assimilation, e.g., an effect on the time, course, rate, amount, extent, or the like of absorption, transport, uptake, or assimilation. A compound or method can also "enhance" transport, uptake, or absorption by any of several pathways, including by increasing the activity, amount, efficiency, binding or other kinetic parameters, of a transport protein involved in the absorption, transport, uptake, or assimilation of a particular amino acid, peptide, or related compound. A compound or method can also enhance absorption, transport, uptake, or assimilation by increasing the rate at which a particular substrate enters the transport molecule, exits the transport molecule, is transported, or by increasing the extent to which a particular substrate is transported over a particular time period, or to a particular endpoint of determination. Any measurable increase in absorption, transport, uptake, or assimilation, whether direct or indirect, as a result attributable to the use of a composition or method, "enhances" the recovery from the physical activity that caused the damage. The terms "improve," "improves," "improving" are synonymous with "enhance" "enhances" and "enhancing," respectively, with respect to any effect on absorption, transport, uptake, or assimilation.

The terms "effective amount" or "amount effective for" mean an amount of a compound, material, composition, medicament, or other material, such as melatonin, that is effective to achieve a particular biological result. Such results include, but are not limited to, one or more of the following: increasing the rate of or extent to which a particular peptide, peptidomimetic or related compound that is taken up from an animal's gastrointestinal lumen into one or more cells lining the gastrointestinal tract, for example, brush border cells. Thus, an effective amount is sufficient to increase the rate or extent of absorption, transport, uptake, assimilation or the like of a transport protein substrate at a particular point in time, or over a particular period of time, relative to a control animal that did not receive an effective amount of the compound. Additional potential results of an effective amount include increasing the amount of an oligopeptide transport protein in one or more cells or cell types. Such an increase can occur by increasing the half-life of the transport protein, e.g., by increasing the rate of production or decreasing the rate of degradation or turn-over of the transport protein. Increases in absorption, transport and the like can also arise from inducing production of the transport protein, e.g., by increasing the rate of transcription or translation of the transport protein in the cell, or by increasing the half-life of an mRNA encoding the transport protein in the cell. An increase can also occur by any combination of the foregoing, and by other means of increasing the amount or activity of a biologically-active protein that are understood by those of skill in the art. In some embodiments herein, an amount of a compound for enhancing or improving absorption of a substrate, such as a peptide, peptidomimetic, or related compound, can be effective when administered or consumed prior to the time of administration of the substrate or compound to be absorbed or transported. In other embodiments, an effective amount can be administered or consumed at the same time as the substrate or compound to be absorbed or transported, separately or as part of the same food composition or formulation, or medicament. In still other embodiments, an effective amount can be administered or consumed within a specified window of time after the consumption of most or all of the substrate or compound to be absorbed or transported. Combinations of the foregoing are possible such that an effective amount can be administered or consumed before, during, or after the consumption or administration of the substrate or compound to be absorbed or transported. The total effective amount can be administered or consumed in more than one portion or dose, and an effective amount can be administered or consumed at more than one time before, during, or after the consumption of the substrate or compound to be absorbed or transported. For various reasons, preferably the effective amount is administered or consumed not later than about 60-120 minutes before or after the consumption or administration of the substrate or compound to be absorbed or transported. Preferably, the effective amount is administered, for example orally, within a period of 1, 5, 10, 15, 20, 30, 40, 45, 50, or 55 minutes, or any intermediate values at less than about 1 hour before the consumption or administration of the substrate or compound to be absorbed or transported. In other embodiments the effective amount is administered or consumed within 60, 70, 80, 90 minutes or less before the consumption or administration of the substrate or compound to be absorbed or transported. In still other embodiment, an effective amount may be consumed within 100, 110, or even 2 hours before the consumption or administration of the substrate or compound to be absorbed or transported. Some influence may accrue by administration outside of this approximately 2 hr window of time before and after the before the consumption or administration of the substrate or compound to be absorbed or transported, however, the skilled artisan will appreciate that the potential benefits decrease as the administration time extends well beyond this window.

The term "antibiotic" means any antibiotic capable of being transported by peptide transporter proteins.

The term "animal" means any animal that could benefit from one or more of the compositions and methods of the invention, particularly an animal that could benefit from methods and compositions that are useful for enhancing, improving, or increasing the in vivo absorption, transport, uptake, assimilation, or the like of di-, tri- and other oligopeptides, peptidomimetics, including amino acid esters of drugs or prodrugs, substrates for intestinal oligopeptide transport proteins, particularly those oligopeptide transport proteins that are located in the gastrointestinal tract of an animal and the activity of which are enhanced, stimulated, or the like, by melatonin or an certain other peptides or hormones. Thus, the invention relates to any animal, preferably a mammal. Unless otherwise specified, or clear from the context, the term "animal" or "mammal" herein includes humans. The term "animal" is used in a general sense and means a human or other animal, including avian, bovine, canine, equine, feline, hicrine, lupine, murine, ovine, and porcine animals. A "companion animal" as used herein means any domesticated animal, and includes, without limitation, cats, dogs, rabbits, guinea pigs, ferrets, hamsters, mice, gerbils, horses, cows, goats, sheep, donkeys, pigs, and the like. Certain embodiments in which human animals are expressly excluded, or clearly excluded by the context, may be preferred herein. In certain embodiments, companion animals are preferred, e.g., dogs and cats.

The term "aging" means that an animal has reached an age that is about 50% of it expected lifespan, i.e., 50% of the expected lifespan for an animal of that type, breed, species, etc. In a preferred embodiment, an aging animal is has attained an age that is at least 60%, 66.6%, 70%, 75%, or 80% of its expected or calculated lifespan based estimates for its type, breed, species, etc.

The terms "food" or "food composition" mean a product or composition that is intended for ingestion by an animal, including a human, and provides nutrition to the animal. The term "food" includes any food, feed, snack, food supplement, treat, meal substitute, or meal replacement, whether intended for a human or another animal. "Food" encompasses such products in any form, solids, liquids, gels, or mixtures or combinations thereof. "Animal food" includes food or feed intended for any domesticated or wild species. In preferred embodiments, a food for an animal represents a nutritionally complete food composition, e.g., a pelleted, extruded, or dry food. Examples of such animal foods include extruded pet foods, such as foods for dogs or cats.

The terms "administering" or "administration" include self-administration in addition to administration to another animal, for example a caretaker may administer a food, composition, medicament, or the like to a companion animal. A caretaker may also ingest or consume a food, composition, medicament or the like, thereby administering that product, composition, or medicament to himself or herself. While administration by any acceptable route is contemplated for use herein, oral administration is presently preferred for many embodiments. It is also preferred that the substrate or compound to be absorbed or transported be administered orally, e.g., consumed as a food, beverage, dietary supplement. Administration can be on a regular basis or can be long-term administration.

The term "regular basis" with respect to the administration of the effective amount for practice of the methods provided herein, or with respect to the administration of the compositions provided herein means the administration, whether before, at the same time as, or after consumption of the substrate or compound to be absorbed or transported, can be repeated periodically. Thus, administration can be at least once daily, or even twice, thrice, or more daily, such as with every feeding. A regular basis can entail administration of an effective amount less frequently, for example, 2 or 3 times per week, or even once weekly. Preferably the administration of the effective amount, for example of melatonin, is at least as frequent as the consumption of the substrate or compound to be absorbed or transported. More frequent dosing or consumption, such as twice or three times weekly, is preferred in certain embodiments. One embodiment features regimens comprising at least once daily administration of an effective amount, even where the consumption of the substrate or compound to be absorbed or transported is less frequent than once daily, or even only occasional, as defined hereinabove.

The term "long-term administration" means periods of repeated administration or consumption in excess of one month in association with repeated consumption of the substrate or compound to be absorbed or transported. Periods of longer than two, three, or four months are preferred for certain embodiments, for example with certain animals requiring optimal protein/amino acid nutrition. For example aging animals or working that must maintain or build muscle mass, or fight catabolic processes that decrease or degrade muscle protein. Also preferred are more extended periods that include longer than 5, 6, 7, 8, 9, or 10 months, especially for populations animals that may benefit from extended or long term administration including aging animals, and animals with nutritional disorders or gastrointestinal diseases, for example malabsorptive disorders. Periods in excess of 11 months or 1 year are also suitable, as are longer term use extending over 1, 2, 3, or more years.

The terms "oral administration" or "orally administering" mean that the animal ingests, or a human is directed to feed, or does feed, the animal one or more of the compositions described herein. Wherein a human is directed to feed the composition, such direction may be that which instructs and/or informs the human that use of the composition may and/or will provide the referenced benefit, for example, enhancing absorption, transport, uptake or assimilation. In some embodiments, the net result is improved protein nutrition in the animal, through improved, increased, or optimized amino acid assimilation. In other embodiments, the intended benefit is the improved distribution of a medicament to an affected animal or tissue or organ within an animal. The direction as to administration may be oral direction (e.g., through oral instruction from, for example, a physician, veterinarian, or other health professional, or radio or television media (i.e., advertisement), or written direction (e.g., through written direction from, for example, a physician, veterinarian, or other health professional (e.g., prescriptions), sales professional or organization (e.g., through, for example, marketing brochures, pamphlets, or other instructive paraphernalia), written media (e.g., interne, electronic mail, website, or other computer-related media), and/or packaging associated with the composition (e.g., a label present on a container holding the composition), or a combination thereof (e.g., label or package insert with directions to access a website for more information).

The term "physical activity" includes any activity that, when engaged in by an animal, tends to reduce or draw down liver and/or muscle glycogen. "Strenuous physical activity" is physical activity that, when engaged in for periods of time or with sufficient frequency, or without sufficient rest, tends to substantially or completely deplete liver and/or muscle glycogen. The skilled artisan will appreciate that the tendency of any activity to partially, substantially or completely deplete glycogen is a function of both the duration and the intensity of the activity. The amount of time (duration) required varies depending on intensity which can be a function of the type of physical activity, the amount of resistance or the amount of muscle work required, whether the activity requires the use of large or small muscle groups or the whole body, the rate at which the activity is performed, and the like. It is evident that most physical activities can become strenuous when engaged in for sufficient time, or with sufficient intensity. Examples of physical activity include various types of work, play, exercise, conditioning, physical skill-development or improvement, rehabilitation, walking, running (or other means or speeds of self-transportation), competitive or noncompetitive sports, and related activities. Many biological functions or processes can also be physically demanding and, thus, constitute physical activity as used herein including giving birth, and "flight or flight" response (i.e., stress response) to physical or psychological stressors, injury and/or healing from trauma, infection, and the like, and many other biological activities. The skilled artisan will appreciate that because of factors such as genetic differences, adaptation, conditioning response, and the like, a physical activity may not be equally strenuous for any two animals, and thus, controlled studies and objective measurements are generally preferable (where suited) to anecdotal evidence or perceived exertion as measures of whether or not a particular activity is strenuous, or whether recovery has been influenced by a particular composition or method.

The term "exercise" means a type of physical activity undertaken by an animal or caused to be undertaken by an animal for a particular purpose such as general heath, fitness, weight management, improving a particular aspect of health or fitness, strengthening, improving a physical skill or set of skills, improving a function, rehabilitating an injury, and the like. Exercise can be performed on a regular basis, e.g., daily, one per week, or twice per week. Frequencies of exercise less than once per week are considered "occasional" exercise. Other patterns of exercise are also recognized and contemplated for use herein.

The terms "in conjunction with" or "in conjunction" mean that an enhancing agent, such as composition for enhancing or improving absorption, transport, uptake, or assimilation of a compound through an intestinal transport protein, or a food composition, medicament, drug, or other compound or composition described herein as having such effect, is administered to an animal (1) together in a food composition or (2) separately, at the same, or different frequency using the same or different administration routes at about the same time or periodically. "Periodically" means that the agent is administered on a dosage schedule acceptable for a specific agent and that the food is fed to an animal routinely as appropriate for the particular animal. "About the same time" generally means that composition for enhancing absorption or transport is administered at the same time or within about 2 hours of the administration or consumption of a substrate or compound to be absorbed or transported. "In conjunction" specifically includes administration schemes wherein an enhancing agent, composition, food, or the like for enhancing or improving absorption, transport, update, or assimilation, as described above, is administered for a predetermined, prescribed, or desired period, and the administration is performed within a defined window of time before, during, or after the administration or consumption of a substrate or compound to be absorbed or transported, including on a regular basis and long-term administration. Preferably the window of time is between about 60 to 120 minutes before the start of and after the completion of the administration or consumption of a substrate or compound to be absorbed or transported.

The term "single package" means that the components of a kit are physically associated, in or with one or more containers, and considered a unit for manufacture, distribution, sale, or use. Containers include, but are not limited to, bags, boxes or cartons, bottles, packages of any type or design or material, over-wrap, shrink-wrap, affixed components (e.g., stapled, adhered, or the like), or combinations of any of the foregoing. For example, a single package kit may provide containers of individual compositions and/or food compositions physically associated such that they are considered a unit for manufacture, distribution, sale, or use. A single package may comprise a container of melatonin, one or more peptides or peptidomimetics, and the like, physically-associated such that they are considered a unit for manufacture, distribution, sale, or use.

The term "virtual package" means that the components of a kit are associated by directions on one or more physical or virtual kit components instructing the user how to obtain the other components, e.g., in a bag or other container containing one component and directions instructing the user to go to a website, contact a recorded message or a fax-back service, view a visual message, or contact a caregiver or instructor to obtain, for example, instructions on how to use the kit, or safety or technical information about one or more components of a kit. Examples of information that can be provided as part of a virtual kit include instructions for use; safety information such as material safety data sheets; poison control information; information on potential adverse reactions; clinical study results; dietary information such as food composition or caloric composition; general information on amino acid, peptide, and/or protein nutrition, absorption, transport, or assimilation in vivo; diseases or disorders that effect amino acid, peptide, and/or protein nutrition, absorption, transport, or assimilation in vivo, including malabsorptive disorders; general information on treatment of muscle tissue loss or preservation of muscle mass including in specialized populations such as working animals, animals subjected to physical exercise or activity, or aging animals; self-help relating to amino acid and protein nutrition, absorption, transport, or assimilation; caregiver information for those caring for animals with modified or altered amino acid and/or protein nutrition requirements, challenges of providing optimal amino acid, peptide, and/or protein nutrition; the use, benefits, and potential side-effects or counter-indications for drugs or peptidomimetic compounds that enhance or improve protein, peptide, or amino acid nutrition, absorption, transport, or assimilation in vivo; and the use, benefits, and potential side-effects or counter-indications for drugs or peptidomimetic compounds that are absorbed through the gastrointestinal tract, or delivered by transport through an intestinal peptide transporter in vivo.

The term "mg/kg" means milligrams per kilogram of an animal's body weight.

All percentages expressed herein are by weight of the composition on a dry matter basis unless specifically stated otherwise. The skilled artisan will appreciate that the term "dry matter basis" means that an ingredient's concentration or percentage in a composition is measured or determined after any free moisture in the composition has been removed.

As used throughout, ranges are used herein in shorthand, so as to avoid having to set out at length and describe each and every value within the range. Any appropriate value within the range can be selected, where appropriate, as the upper value, lower value, or the terminus of the range.

The term "about" indicates that the given value, plus or minus 10%, is intended. "About" is thus used a shorthand to reflect the recognition that small variations from the literal value stated are still within the scope of the invention.

As used herein and in the appended claims, the singular form of a word includes the plural, and vice versa, unless the context clearly dictates otherwise. Thus, the references "a", "an", and "the" are generally inclusive of the plurals of the respective terms. For example, reference to "a puppy", "a method", or "a food" includes a plurality of such "puppies", "methods", or "foods". Reference herein, for example to "an antioxidant" includes a plurality of such antioxidants, whereas reference to "pieces" includes a single piece. Similarly, the words "comprise", "comprises", and "comprising" are to be interpreted inclusively rather than exclusively. Likewise the terms "include", "including" and "or" should all be construed to be inclusive, unless such a construction is clearly prohibited from the context. Where used herein "examples," or "for example," particularly when followed by a listing of terms, is merely exemplary and illustrative, and should not be deemed to be exclusive or comprehensive.

The methods and compositions and other advances disclosed here are not limited to particular methodology, protocols, and reagents described herein because they may be varied in ways that are apparent the skilled artisan. Further, the terminology used herein is for the purpose of describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the present invention, certain preferred compositions, methods, articles of manufacture, or other means or materials are described herein.

All patents, patent applications, publications, technical and/or scholarly articles, and other references cited or referred to herein are in their entirety incorporated herein by reference to the extent allowed by applicable law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved. Full citations for publications not i cited fully within the specification are set forth at the end of the specification.

The Invention

The present invention provides compositions and methods useful for enhancing, improving, or increasing the absorption, transport, uptake, and/or assimilation of a peptide, a peptidomimetic, or other gastrointestinal transport protein substrates, e.g., an oligopeptide transporter of the PTR2 family such as PepT1. The compositions and methods have beneficial applications in supporting and/or improving gastrointestinal health, promoting the health or wellness of an animal, providing improved amino acid nutrition to animals with malabsorptive disorders, delivering drugs or prodrugs that are substrates for a gastrointestinal transport protein or modified to be substrates for such a transport protein, and improving or maintaining muscle mass, e.g., in an aging animal or an animal subjected to strenuous physical activity such as exercise. The methods and composition are also useful in any situation where optimal protein and/or amino acid nutrition or assimilation contributes to the overall health of the animal.

In one aspect, the invention provides methods for enhancing transport of peptides, peptidomimetics, or other gastrointestinal transport protein substrates in an animal. The methods comprise administering an amount of a hormone effective for increasing peptide transport through an intestinal transport protein in the animal. In a preferred embodiment the hormone is a non-peptide hormone, preferably melatonin. The hormone can be administered using any route, preferably by oral administration. In one embodiment, melatonin is formulated into or applied onto a food composition designed for consumption by an animal. The food composition can be fed to the animal at any time, including just before the animal's normal sleeping time. In an embodiment, the effective amount of melatonin can be sufficient to induce sleep or drowsiness in the animal. In another embodiment, the effective amount of melatonin is an amount that does not induce sleep or drowsiness in the animal. In various embodiments, the food composition is administered in conjunction with a drug, prodrug, or medicament. The absorption of the drug, prodrug, or medicament is enhanced by the melatonin or other hormone in the food composition.

The invention is based upon the surprising discovery that melatonin enhances, improves, or increases the absorption, transport, uptake, and/or assimilation of peptides, peptidomimetics, and other gastrointestinal transport protein substrates in an animal. Melatonin enhances or increases absorption, transport, uptake, of assimilation of such substrates through intestinal oligopeptide transport proteins. These substrates include, but are not limited to certain drugs, prodrugs, and medicaments, e.g., antibiotics and other drugs or prodrugs that are substrates for oligopeptide transporter proteins in an animal's intestine.

In certain embodiments, the intestinal transport protein is a member of the PTR2 family of membrane transporters. Oligopeptide transporters of the gastrointestinal tract are known in the art. Presently preferred is the Peptide Transporter 1 (PepT1) protein.

The melatonin can be administered in any amount effective for enhancing transport of peptides, peptidomimetics, and other gastrointestinal transport protein substrates in an animal. In one embodiment, the amount of melatonin administered to the animal is at least about 0.1 mg/kg, preferably about 0.5 mg/kg, most preferably 1 mg/kg. In certain embodiments, the amount of melatonin can be 2, 3, 4, or 5 mg/kg. In other embodiments, the amount of melatonin may be as high as 6, 7, 8, 9, or even 10 or more mg/kg. Typically, the melatonin is administered to the animal in amounts of from about 0.5 mg/kg to about 50 mg/kg, preferably from about 1 mg/kg to about 25 mg/kg. When administered in a food composition, the melatonin can be administered one to three hours before the animal's normal sleep time. In such embodiments, melatonin's natural ability to induce sleep or drowsiness may aid a sick or stressed animal in recovering a more healthful status through improved rest, improved nutrition, and improved absorption/delivery of a medicament such as an antibiotic.

Oral administration of melatonin, even well in advance of administering a gastrointestinal transport protein substrate, increases the rate of substrate transport and absorption in the animal and the total amount of substrate absorbed. Moreover, the effect can be accomplished in certain cases without inducing drowsiness or sleep in the animal, despite melatonin's widely-known function. Thus, in one embodiment, the amount of melatonin does not induce sleep, or drowsiness in the animal. The skilled artisan will appreciate that such embodiments are more useful when the food compositions are to be given, for example, as a first meal after the animal wakes from sleep, or during the midst of the animal's wake cycle, so as not to disrupt or perturb the animal's diurnal rhythm. For such embodiments, the amount of melatonin administered is less than about 3 mg/kg, preferably less than about 1 mg/kg.

In one embodiment, the enhanced intestinal transport is accomplished through an increase in the activity of the gastrointestinal transport protein. The skilled artisan will appreciate that the activity of the transport protein can comprise several aspects that collectively define the transport of a substrate from the gut lumen into the cells lining the lumen. Thus any one or more of the rate of peptide transport, the affinity of the transport protein for one or more peptides, or the efficiency of the transport protein, or the total extent or amount or the substrate transported are considered for purposes herein as aspects of the activity of the transport protein.

In one embodiment, melatonin is administered in conjunction with one or more peptides, peptidomimetics, or other gastrointestinal transport protein substrates. In certain embodiments, the method enhances absorption of the substrate while in other cases the peptide may itself be a further enhancer of absorption, e.g., a peptide that stimulates transport through an intestinal transport protein.

The methods are very useful where the peptide, peptidomimetic, or substrate provides a nutrient or medicament. In some cases, the peptidomimetic is a medicament such as an antibiotic or other drug. These methods are particularly useful where an expensive or life-saving drug is difficult to safely get into a patient because the drug is poorly absorbed.

Where the peptide, peptidomimetic, or substrate is a nutrient, the methods are particularly useful where the animal has a malabsorptive disorder. Persons skilled in the art of nutritional disorders or gastrointestinal diseases will appreciate that a variety of such disorders are known. It can be very complicated to provide an animal afflicted with a malabsorptive disorder with adequate nutrition on a regular basis.

In certain embodiments, melatonin is administered in conjunction with one or more stimulants such as caffeine, nicotine, ephedrine, amphetamines, ampakines, or the like. Such embodiments may be most useful where it is vital that the animal not experience drowsiness, or perhaps where the animal requires a larger dose of melatonin to obtain the full benefits of enhanced absorption.

In various embodiments, the animal is a human; non-human such as a cow, horse or pig; or companion animal such as a dog or cat.

In a further aspect, the invention provides compositions comprising melatonin and one or more peptides, peptidomimetics, and other gastrointestinal transport protein substrates. In one embodiment, at least one of the peptides, peptidomimetics, or substrates is transported in the animal's gastrointestinal tract via an intestinal peptide transporter whose activity is enhanced, increased or improved by melatonin. The composition is preferably a comestible composition that is suitable for oral consumption. In one embodiment, the melatonin and the substrates (e.g., peptides and/or peptidomimetics) are combined into a single dosage form, e.g., a pill or capsule. In another embodiment, the melatonin and the substrate are in a controlled release or time release formulation.

In one embodiment, at least one peptidomimetic comprises a beta lactam ring. In preferred embodiments, the peptidomimetic comprises a penicillin, a cephalosporin, a monobactam, a carbapenem, a β-lactamase inhibitor, a derivative or a salt of any of the foregoing, or any combination thereof. In another embodiment, the peptidomimetic comprises an antibiotic, an antihypertensive, or an antiviral drug or prodrug.

In another aspect, the invention provides methods for decreasing the amount of antibiotic required to combat an antibiotic sensitive microorganism, e.g., prevent or treat an infection, disease, or other medical condition for which antibiotics would normally be prescribed. The methods comprise orally administering one or more antibiotics in conjunction with an amount of melatonin effective for enhancing transport of the antibiotics by gastrointestinal transport proteins. The melatonin increases the amount of antibiotic transported into the animal via gastrointestinal transport proteins in a given time and therefore decreases the amount of antibiotic that needs to be administered to an animal to effect the antibiotic's purpose, e.g., combat an infection. Using less antibiotic decreases the cost of the antibiotic needed to combat the microorganism and &creases the likelihood of any adverse side effects caused by antibiotic administration. Further, using less antibiotics reduces the risk of developing antibiotic resistant microorganisms. Basically, the same result can be obtained with less antibiotic if the antibiotic is administered in conjunction with melatonin.

In another aspect, the invention provides methods for increasing the efficacy of a given amount or dosage of antibiotic administered to an animal to combat an antibiotic sensitive microorganism. The methods comprise administering one or more antibiotics in conjunction with an amount of melatonin effective for enhancing transport of the antibiotics by gastrointestinal transport proteins. The melatonin increases the amount of antibiotic transported into the animal via gastrointestinal transport proteins in a given time. This increases the efficacy by getting more antibiotic into the animal where it can kill the microorganism. Increasing the efficacy of a given amount of antibiotic means that an infection, disease, or other condition caused by an antibiotic sensitive microorganism will have less adverse effect on the animal. Thus, two animals with the same infection will recover at different rates and have different symptoms. An animal administered an antibiotic with melatonin will recover from an infection in less time than an animal administered an antibiotic alone. Similarly, an animal administered an antibiotic with melatonin will have less adverse symptoms than an animal administered an antibiotic alone, e.g., less fever, chills, nausea, vomiting, cramps, pain, fatigue, malaise, or other symptoms characteristic of a particular infection or disease. Further, more effective antibiotics also help reduce the risk for further complications from infection or disease, e.g., sepsis. Basically, a much better result can be obtained with the same amount of antibiotic if the antibiotic is administered in conjunction with melatonin.

In another aspect, the invention provides methods for reducing the likelihood of complications developing from an infection or disease caused by an antibiotic sensitive microorganism. The methods comprise administering one or more antibiotics in conjunction with an amount of melatonin effective for enhancing transport of the antibiotics by gastrointestinal transport proteins. When melatonin is administered in conjunction with the antibiotic, more antibiotic is transported into the body where it can combat the microorganism that would have been transported into the body if the antibiotic had been administered alone. This additional amount is available to combat the microorganism and reduce the likelihood that the microorganism will cause complications, e.g., sepsis or chronic disease.

In another aspect, the invention provides methods for decreasing the risk of developing an antibiotic resistant microorganism. The methods comprise orally administering one or more antibiotics in conjunction with an amount of melatonin effective for enhancing transport of the antibiotics by gastrointestinal transport proteins. The melatonin increases the amount of antibiotic transported into the animal via gastrointestinal transport proteins and therefore decreases the amount of antibiotic required to affect its purpose, i.e., lowers the required dosage. When administered in conjunction with melatonin, the amount of antibiotic administered to an animal to effect its purpose can be less and/or the frequency of administration can be decreased. Basically, it takes less antibiotic to treat an infection or other condition requiring antibiotics because more antibiotic is absorbed from the intestines in a given time due to enhanced transport of the antibiotic by the gastrointestinal transport proteins. Using less antibiotics overall puts less antibiotics into the environment and decreases the opportunity for the development of antibiotic resistant microorganisms, particularly infective microorganism such as *Staphylococcus aureus* or *Enterococcus faecium*.

When administered in conjunction with antibiotics, the melatonin is administered in an amount suitable for increasing the absorption of the antibiotic from the intestine into the blood stream of the animal. Generally, melatonin is administered in amounts of at least about 0.1 mg/kg, preferably about 0.5 mg/kg, most preferably 1 mg/kg. Typically, the melatonin is administered to the animal in amounts of from about 0.5 mg/kg to about 50 mg/kg, preferably from about 1 mg/kg to about 25 mg/kg. The antibiotic is any antibiotic useful for preventing or treating a disease or condition caused by a microorganism affected by the antibiotic. In various embodiments, the antibiotic is a penicillin, a cephalosporin, a monobactam, a carbapenem, a β-lactamase inhibitor, a derivative or a salt of any of the foregoing, or any combination thereof.

In another aspect, the invention provides methods for improving absorption of a PepT1 substrate in the gastrointestinal tract of an animal. The methods comprise administering to the animal an amount of melatonin effective for improving absorption of the PepT1 substrate. In one embodiment, the amount of melatonin does not induce sleep or drowsiness in the animal. Where the amount of melatonin is sufficient to induce sleep or drowsiness, the methods are preferably applied within about, one, two, or three hours of the animal's normal sleeping period, so that any induced sleep or drowsiness will naturally lead into the animal's normal twilight or sleep period so as to not substantially disrupt the animal's established diurnal cycle. In another embodiment, the PepT1 substrate that is the subject of the method and whose absorption is to be improved, is a dipeptide, tripeptide, or a peptidomimetic as defined hereinabove. In various embodiments, the PepT1 substrate comprises a tryptophan, glutamine, arginine, or a branched-chain amino acid residue. Among the branched-chain amino acids, valine is sometimes preferred. In a preferred embodiment, the method further comprises administering the melatonin in conjunction with at least one PepT1 substrate.

In various embodiments, the PepT1 substrate whose absorption is to be improved or enhanced is useful for any of a variety of specific or general conditions relating to the animal's health or well-being. In one embodiment, the PepT1 substrate is useful for promoting optimal protein/peptide/amino acid nutrition, absorption, or assimilation in an aging animal. Such embodiments are useful for preserving muscle tissue, building muscle mass, or reversing or slowing catabolic results of aging on muscle protein. In another embodiment, the PepT1 substrate helps promote optimal protein/peptide/amino acid nutrition, absorption, or assimilation where the animal has a malabsorptive disorder. In some embodiments, the melatonin is administered orally in one or more doses. One or more of the doses are preferably provided in conjunction with a PepT1 substrate.

The melatonin is preferably present in a food formulated for consumption prior to the animal's normal sleeping time in some embodiments. Such embodiments tend to employ larger doses or amounts of melatonin, such that the melatonin may induce drowsiness, a twilight state, or even profound sleep in the animal. In one embodiment, the amount of melatonin is between about 1 to 10 mg/kg. Amounts of 5 to 10 mg/kg are more preferred for such embodiments. Amounts of melatonin of about 1 mg per kg or less are preferred for embodiments where it is not desirable or useful to induce sleep or drowsiness. The methods and compositions can also be practiced/administered in conjunction with one or more stimulants to overcome possible drowsiness effects in sensitive animals. Thus, caffeine and similar stimulants are suitable for use herein.

In another aspect, the invention provides methods for improving the absorption of a peptidomimetic in an animal. The methods are particularly of use in improving the delivery, absorption, or application of certain drugs and prodrugs in vivo. The methods comprise administering in conjunction to the animal, in one or more doses, an amount of melatonin effective for improving the absorption of the peptidomimetic and the peptidomimetic. The steps can be ordered in any fashion. In presently preferred embodiments, the amount of melatonin can be administered without inducing sleep or drowsiness in the animal.

In preferred embodiments, the melatonin is administered orally in one or more doses. One of the advantages of the instant methods is that oral administration of compounds such as melatonin or its precursors, provides a safe, economical, effective, and simple way of improving the delivery, and absorption, transport, or uptake, and thus, the effectiveness of a given dose or amount of certain drugs by allowing more active component ultimately to be present in the animal's cells and/or circulatory systems. Thus, in some embodiments, at least one of the one or more doses is administered prior to, or in conjunction with, administering the peptidomimetic.

The peptidomimetic comprises an antibiotic or other drug or prodrug in various embodiments. Peptidomimetics comprising a β-lactam ring are useful herein. B-lactam ring-containing antibiotics are particularly useful herein, for example, a penicillin, a cephalosporin, a monobactam, a carbapenem, a β-lactamase inhibitor, a derivative or a salt of any of the foregoing, or any combination thereof.

In other embodiments, the peptidomimetic is an amino acid modification, such as an amino acid ester, of a drug or prodrug. The skilled artisan will appreciate that certain drugs or classes of drugs are oligopeptides, or contain peptide or peptide-like structures. Many such compounds are known to be substrates for intestinal peptide transport proteins. Other drugs can be modified, for example by manufacture as a prodrug that is converted in vivo into the active drug. In some cases the drug prodrug is or contains sufficient structure to be a substrate for an intestinal transport protein. In other cases, esterifying an amino acid can be sufficient to confer status as a substrate for an intestinal oligopeptide transporter. Presently, antihypertensive drugs and antiviral drugs are preferred for use with the methods disclosed herein, in addition to antibiotics discussed above.

In yet another aspect, the invention provides methods for enhancing the nutritive value of a food composition in vivo. The methods comprise administering the food composition to an animal in conjunction with an amount of melatonin sufficient for enhancing absorption of one or more di-or tripeptides present in the food or its natural digestion products in the animal.

In one embodiment, the method is adapted to situations wherein the animal will benefit from improved protein nutrition, or amino acid assimilation. In some embodiments the animal is a working animal, or an animal that is subjected to strenuous physical activity or exercise. In another embodiment, the animal is an aging animal. The animal has a malabsorptive disorder in another embodiment. In yet others, the animal is undergoing stress from a disease.

In certain embodiments, the method is practiced with amounts of melatonin that do not induce sleep or drowsiness, such as doses or amounts not exceeding about 1 mg/kg. In other embodiments, the amount of melatonin may induce sleep or drowsiness and the melatonin is administered within about 1, 2, or 3 hours prior to the animal's normal sleeping time, or any time so as not to substantially disrupt the animal's diurnal cycle.

In a further aspect, the invention provides kits suitable for improving the transport of a substrate through a gastrointestinal transport protein. The kits comprise, in separate containers in a single package, or in separate containers in a virtual package, as appropriate for the kit component, melatonin and at least one other component that is (1) a peptidomimetic; (2) a di- or tri-peptide; (3) an oligopeptide; (4) an amino acid ester of a drug or prodrug; (5) another gastrointestinal transport protein substrate; or (6) a further ingredient suitable for consumption by an animal, and (7) instructions or further information for using the melatonin and with the at least one other component to improve the transport of a substrate through a gastrointestinal transport protein in an animal.

In one embodiment, the instructions indicate that the kit can be used in a manner so as not to substantially disturb or disrupt the animal's diurnal cycle. In one embodiment, the instructions teach the user how to use the kit in a manner that does not induce sleep or drowsiness in the animal. For example, the instructions may indicate that to avoid drowsiness, the animal should not receive more than a particular dose or amount of melatonin, such as about 1 mg/kg melatonin. In another embodiment, at least a portion of the instructions or further information is provided virtually.

In another aspect, the invention provides a means for communicating information about, or instructions for use of, one or more of (a) methods for enhancing transport of a peptide in an animal; (b) methods for improving absorption of a PepT1 substrate in the gastrointestinal tract of an animal; (c) methods for improving absorption of a peptidomimetic in an animal; (d) methods for enhancing the nutritive value of food in vivo, (e) compositions comprising melatonin and one or more peptides, peptidomimetics, and other gastrointestinal transport protein substrates; (f) kits comprising the components need to practice the methods, or (g) making or using the methods, compositions, or kits disclosed herein.

In one embodiment, the aforesaid means comprises a web site, visual display kiosk, printed matter, brochure, product label, package insert, advertisement, handout, public announcement, audiotape, videotape, DVD, CD-ROM, computer-readable chip, computer-readable card, computer-readable disk, computer memory, or combination thereof.

In another aspect, the invention provides a package comprising a label device indicating that melatonin can be used to enhance the absorption of peptides, peptidomimetics, or other gastrointestinal transport protein substrates. In various embodiments the substrates are PepT1 substrates, including di- and tri-peptides; peptidomimetics, including amino acid esters of drugs or prodrugs; antibiotics; and combinations thereof. The label can be any word or words, picture, design, acronym, slogan, phrase, or other device, or combination thereof, that indicates that melatonin can be used to enhance the absorption of a PepT1 substrate. Typically, such device comprises the words "enhances antibiotic absorption" or "enhances absorption of peptides" or an equivalent expression printed on the package. Any package or packaging material suitable for containing melatonin is useful in the invention, e.g., a bag, box, bottle, can, pouch, and the like manufactured from paper, plastic, foil, metal, and the like. In a preferred embodiment, the package contains a food composition comprising melatonin, preferably a human or companion animal food composition.

In another aspect, the invention provides methods for promoting the health and/or wellness of an animal. The methods comprise administering to the animal a health or wellness promoting amount of melatonin and one or more peptides, peptidomimetics, or other gastrointestinal transport protein substrates. The melatonin and substrates can be administered in any suitable manner, preferably orally, most preferably orally in a food composition. The melatonin and substrates can be administered in a single dosage form or can be administered in conjunction. The melatonin is administered in amounts or at least about 0.1 mg/kg, preferably about 0.5 mg/kg, most preferably 1 mg/kg. Typically, the melatonin is administered to the animal in amounts of from about 0.1 mg/kg to about 50 mg/kg, preferably from about 1 mg/kg to about 25 mg/kg.

In another aspect, the invention provides methods for promoting the health and/or wellness of an animal. The methods comprise administering to an animal a health or wellness promoting amount of melatonin in conjunction with one or more peptides, peptidomimetics, and other gastrointestinal transport protein substrates. The melatonin increases the absorption of these substrates by the animal. The animal uses these substrates promote the well being of the animal, e.g., to combat disease (antibiotics) and build lean body mass (peptides).

In another aspect, the invention provides methods for increasing lean body mass in an animal. The methods comprise administering melatonin in conjunction with peptides, peptidomimetics, or other gastrointestinal transport protein substrates that are useful for building lean body mass in a animal, e.g., di- and tripeptides. The substrates can be dietary supplements, individual compounds, or can be obtained by the animal from a food composition or by digestion thereof.

In a further aspect, the invention provides for a medicament that comprises a composition having melatonin and at least one of (1) a peptidomimetic; (2) a di- or tri-peptide; (3) an oligopeptide; (4) an amino acid ester of a drug or prodrug; or (5) another gastrointestinal transport protein substrate. The medicament is prepared using methods standard in the preparation of pharmaceutical compositions. The medicament is prepared using pharmaceutically-acceptable excipients, diluents, carriers, extenders, salts and the like.

In various embodiments the medicament comprises a composition comprising melatonin and a peptidomimetic that is an antibiotic, an antihypertensive, or an antiviral. In another embodiment, the peptidomimetic comprises a beta lactam ring, and can be a penicillin, a cephalosporin, a monobactam, a carbapenem, a β-lactamase inhibitor, a derivative or a salt of any of the foregoing, or any combination thereof. In one embodiment, the medicament comprises melatonin and a beta lactam antibiotic.

For all aspects of the invention, the peptides, peptidomimetics, and other gastrointestinal transport protein substrates are administered to the animal in amounts suitable for the appropriate peptide, peptidomimetic, or substrate and its intended purpose. Such amounts are discernable by the skilled artisan. Similarly, the skilled artisan can determine the amount of melatonin to be administered based upon the knowledge in the art and the disclosure herein.

These and other aspects of the invention may be further illustrated by the following examples. It will be understood that these examples are provided for purposes of illustration of specific aspects, and thus, they do not limit the scope of the invention disclosed herein as a whole, unless otherwise specifically indicated.

EXAMPLES

Example 1

A study was conducted to assess the ability of 5-methoxy-N-acetyltryptamine (melatonin in the examples) to improve absorption of small peptides and/or peptidomimetics.

Methodology: The study was designed to test the feeding of melatonin on the absorption of cephalexin. Dogs (n=24, Body Weight (BW) range: 7-14 kg, age range: 1.5 to 14 yrs)

were divided into a test group and a control group. The respective groups were balanced for gender.

The test group received a single dose of melatonin (1 mg/kg BW) at 12:00 pm, followed by a single dose of cephalexin (15 mg/kg BW) between 1:00 and 2:00 pm. Dosing with melatonin and cephalexin were both by oral administration to the dogs. The study evaluated cephalexin absorption by determining the pharmacokinetics of cephalexin appearance in serum subsequent to the melatonin administration. The control group received cephalexin at the same time as the test group, but they did not receive oral melatonin. Samples for pharmacokinetic analysis were taken at 15, 30, 45, and 60 min, as well as 1.5, 2, 2.5, 3, 3.5, 4, 6, and 8 hours after oral dosing of cephalexin. Cephalexin concentration was determined by high pressure liquid chromatograph. Serum melatonin content was analyzed before and after the oral administration time, e.g., at −5, −3, −1, −0.5 hour before, 0 (dosing time), and at 0.5, 1, 2, 3, 4, and 6 hours after oral dosing of melatonin. Melatonin was quantified by radioimmunoassay procedures. The results are shown in Tables 1, 2, and 3.

Referring to Tables 1, 2, and 3, the data show that oral administration of melatonin increased the absorption of cephalexin. The data for cephalexin pharmacokinetics are shown in Table 1. The data demonstrate the appearance and disappearance of cephalexin in dog serum in the time (hrs) post-administration. Analysis of mean blood concentration data at each time point shows that amounts were statistically different ($P<0.05$) at all times from 2.0 h through 6 h after dosing. Pharmacokinetic data were used to calculate the rate of appearance and peak height, shown in Table 2, which was analyzed for differences. Calculated levels of cephalexin for the group receiving melatonin supplementation peaked 8.8% higher than those for the group that did not receive melatonin ($P=0.05$; Table 2). Based on mean pharmacokinetic concentration data, shown in Table 1, cephalexin levels at 2 hours (time of peak) after dosing were 19% greater in dogs receiving melatonin supplementation. In addition, total absorption capacity (as determined from total area under the curve) was increased ($P=0.03$) by 10.6% in dogs receiving melatonin.

As can be seen in Table 3, in dogs that ingested melatonin, melatonin appearance in serum increased significantly for up to 6 hours after ingestion. Control group dogs, which were not administered melatonin, had baseline levels. The standard error (SE) of each treatment mean is also shown in Table 3.

TABLE 1

Cephalexin Pharmacokinetic Data: Serum Concentration (μg/mL) of Cephalexin in Dogs Following Cephalexin Oral Dosing, With or Without Oral Melatonin Ingestion Treatment

| Time | Melatonin | Control | SE |
|---|---|---|---|
| 0.25 | 0.86 | 0.79 | 0.5 |
| 0.50 | 3.80 | 4.17 | 0.8 |
| 0.75 | 7.28 | 8.19 | 1.1 |
| 1.00 | 10.34 | 10.91 | 1.3 |
| 1.50 | 15.12 | 13.87 | 0.8 |
| 2.00 | 16.34 | 13.73 | 0.7 |
| 2.50 | 15.40 | 14.31 | 0.3 |
| 3.00 | 14.33 | 13.00 | 0.4 |
| 3.50 | 12.78 | 11.80 | 0.4 |
| 4.00 | 11.66 | 9.90 | 0.4 |
| 6.00 | 6.93 | 5.91 | 0.3 |
| 8.00 | 3.74 | 3.73 | 0.3 |

TABLE 2

Peak Cephalexin Concentration in Dogs After Cephalexin Dosing With and Without Oral Melatonin Ingestion

|  | Melatonin | Control | SE |
|---|---|---|---|
| Peak height | 17.3 | 15.9 | 0.5 |
| Rate of increase | 9.3 | 7.6 | 0.7 |
| Total area under curve | 78.0 | 70.5 | 2.5 |

TABLE 3

Melatonin Pharmacokinetic Data: Serum Concentration (pg/mL) of Melatonin in Dogs With or Without Oral Melatonin Ingestion

| Time of Day | Melatonin | SE | Control | SE |
|---|---|---|---|---|
| 9:00 am | 3.9 | 3.18 | 0.3 | 0.05 |
| 11:00 am | 0.5 | 0.11 | 0.2 | 0.04 |
| 12:00 pm | 18.4 | 7.81 | 0.3 | 0.04 |
| 12:30 pm | 10698.3 | 2669.48 | | |
| 1:00 pm | 9552.5 | 1547.78 | | |
| 1:30 pm | 8974.0 | 1789.28 | | |
| 2:00 pm | 4785.4 | 895.36 | 0.3 | 0.03 |
| 3:00 pm | 1458.7 | 264.25 | | |
| 4:00 pm | 746.7 | 220.37 | 0.2 | 0.02 |
| 5:00 pm | 273.3 | 80.88 | | |
| 7:00 pm | 88.5 | 14.84 | 0.6 | 0.16 |

Example 2

Method for Increasing Amino Acid Absorption in Animals by Oral Administration of Melatonin or its Precursors. A study was conducted to titrate the dose of orally administered melatonin to improve absorption of small peptides and/or peptidomimetic drugs. Peptidomimetic drugs, like cephalexin, and small peptides (di- and tri-peptides) are absorbed by a single small intestinal transport protein, Peptide Transporter 1.

Methology: The study used n=40 Labrador Retriever dogs (BW range: 21-40 kg) to test the oral ingestion of melatonin compared to no-melatonin placebo control on the absorption of cephalexin, an antibiotic that also serves as a marker substrate for small peptides. The dogs were balanced for gender and the ages ranged from 1.5 to 9 years old. The study evaluated cephalexin absorption by orally administering a single 15 mg/kg BW dose of cephalexin to dogs at 2:00 pm, and subsequently determining the pharmakinetics of cephalexin appearance in serum. Dogs were randomized into 5 different treatment groups and received a single oral dose of melatonin (0.01, 0.1, 1, or 3 mg/kg BW) in a gelatin capsule or placebo simultaneously as the cephalexin dose. The oral dose was immediately followed by an oral administration of 60 mL of water by a 60 mL irrigation syringe. The melatonin dose diluent and placebo pill were the inert carrier, avicel. Cephalexin pharmakinetics were analyzed at 30 and 60 min after dosing and 1.5, 2, 2.5, 3, 4, and 6 hours after oral dosing of cephalexin. Cephalexin concentration was determined by high pressure liquid chromatograph.

In addition, day/night activity data was collected for 72 hours to determine if oral administration of melatonin resulted in decreased activity. Dogs were fitted with an Actiwatch monitor 24 hours before oral ingestion of one of the melatonin doses, specifically at 2 PM on day 1. Following the oral administration of melatonin, the activity monitoring continued for another 48 hours, at which time the monitors were removed and the data collected for analysis. The dogs were exposed to 11.5 h light:12.5 h dark cycle, in which kennel lighting and natural light was combined over the 11.5 hour period. In the morning the light cycle began with exposure to kennel lighting at 6 AM and darkness onset occurred at 5:30 PM with sunset. For data analysis, activity was separated into three periods of time, afternoon light phase (2 PM to 5:30 PM, 3.5 h duration), dark phase (5:30 PM to 6 AM, 12.5 h duration), and morning light phase (6 AM to 2 PM, 8 h duration). For data analysis purposes, a 24 hour period is from 2:00 PM to 1:59 PM. The results are discussed below.

Cephalexin Absorption and Appearance Data: Oral administration of melatonin demonstrated an increase in the absorption of cephalexin in dogs dosed 0.1, 1, and 3 mg/kg BW compared to placebo dogs. The data below provides evidence of this effect, which includes the mean pharmakinetic data, peak height, rate of serum appearance, and total cephalexin appearance as total area under the curve. Cephalexin pharmakinetic data is presented in Table 4, which demonstrates the appearance and disappearance of cephalexin in dog serum. Analysis of mean blood concentration data at each time point indicated that administering 3 mg/kg BW resulted in an increase in the appearance of cephalexin. Specifically, at 1 h after dosing cephalexin levels were 82.8% greater, 52% greater at 1.5 h after, 32.6% greater at 2 h after, 19.4% greater at 2.5 h after, and finally 9.1% greater at 3 h after. Administering melatonin orally at the 0.1 and 1 mg/kg BW dose also resulted in an increase of cephalexin appearance in blood compared to the placebo group, but the increase was not as great. Specifically, at 1 h after dosing cephalexin levels were 34 to 22.6% greater, 25% greater at 1.5 h after, 18 to 19.5% greater at 2 h after, and 14.3 to 17.5% greater at 2.5 h after. Similar to dosing 3 mg/kg, levels at 3 h after dosing were 9% greater. When 0.01 mg/kg BW melatonin was orally administered the amount of cephalexin appearing in the blood was slightly decreased compared to the placebo group.

TABLE 4

Cephalexin Pharmakinetic Data: Serum Concentration (ug/mL) of Cephalexin in Dogs Following Cephalexin Oral Dosing with or without Oral Melatonin Dose (mg/kg BW) Melatonin Treatment

| Time (hour) | placebo | 0.01 mg/kg BW | 0.1 mg/kg BW | 1 mg/kg BW | 3 mg/kg BW |
|---|---|---|---|---|---|
| 0.50 | 2.01 | 2.57 | 3.24 | 1.80 | 2.89 |
| 1.00 | 6.28 | 7.19 | 8.43 | 7.70 | 11.48 |
| 1.50 | 9.92 | 9.03 | 12.39 | 12.40 | 15.08 |
| 2.00 | 11.77 | 10.61 | 13.89 | 14.07 | 15.61 |
| 2.50 | 12.35 | 10.65 | 14.12 | 14.51 | 14.74 |
| 3.00 | 12.22 | 10.24 | 13.38 | 13.63 | 13.33 |

TABLE 4-continued

Cephalexin Pharmakinetic Data: Serum Concentration (ug/mL) of Cephalexin in Dogs Following Cephalexin Oral Dosing with or without Oral Melatonin Dose (mg/kg BW) Melatonin Treatment

| Time (hour) | placebo | 0.01 mg/kg BW | 0.1 mg/kg BW | 1 mg/kg BW | 3 mg/kg BW |
|---|---|---|---|---|---|
| 4.00 | 11.31 | 8.99 | 11.14 | 11.20 | 10.72 |
| 6.00 | 7.57 | 5.49 | 6.62 | 6.58 | 5.39 |

Referring to Table 5, pharmakinetic data was used to calculate the rate of appearance, peak height, and time of peak. Peak appearance in the blood was 19%, 11.6, and 22.8% greater with an oral dose of melatonin at 0.1, 1, and 3 mg/kg BW, respectively, compared to the placebo group. In addition, the rate of cephalexin appearance was also greater with these three dose levels compared to the placebo. Specifically, the rate was 40, 25.4, and 58.5% greater with 0.1, 1, and 3 mg/kg BW, respectively. Correspondingly, the time to achieve peak appearance also occurred earlier in the groups receiving the oral dose of melatonin, in which the 0.1 mg/kg group was approximately 15 min, 1 mg/kg group was approximately 30 min, and the 3 mg/kg group was approximately 60 min earlier.

TABLE 5

Rate and Peak Appearance of Cephalexin in Dogs After Cephalexin Dosing with and without Oral Melatonin Dose (mg/kg BW) Melatonin Treatment

| | Placebo | 0.01 mg/kg BW | 0.1 mg/kg BW | 1 mg/kg BW | 3 mg/kg BW |
|---|---|---|---|---|---|
| Peak height | 13.3257 | 12.0960 | 15.8500 | 14.8700 | 16.3629 |
| Rate of increase | 5.6598 | 5.8470 | 7.9165 | 7.0783 | 8.9650 |
| Time of peak appearance | 2.7857 | 2.3000 | 2.5000 | 2.2500 | 1.9286 |

The final measure of cephalexin absorption is the assessment of total cephalexin absorption capacity as total area under the curve (AUC). The accumulative AUC of cephalexin at each time period following dosing is compiled, shown in Table 6. In addition, the relative percent change in AUC compared to the placebo group is also included in Table 6. Similar to previous variables tested, the AUC for 0.1, 1, and 3 mg/kg groups was greater at most time points compared to the placebo group. In summary, the 3 mg/kg BW group had the greatest increase for the longest duration of cephalexin absorption capacity compared to the placebo group, in which the AUC was 45 to 34% greater from 1 to 2.5 h after dosing.

TABLE 6

Area Under the Curve for Cephalexin in Blood of Dogs after Cephalexin Dosing with and without Oral Melatonin Dose (mg/kg BW) Melatonin Treatment and Change From Placebo Group

| Time (hour) | Placebo | 0.01 mg/kg BW | % increase of 0.01 mg/kg BW vs placebo | 0.1 mg/kg BW | % increase of 0.1 mg/kg BW vs placebo | 1 mg/kg BW | % increase of 1 mg/kg BW vs placebo | 3 mg/kg BW | % increase of 3 mg/kg BW vs placebo |
|---|---|---|---|---|---|---|---|---|---|
| 0.5 | 0.50 | 0.64 | 28.0% | 0.81 | 62.0% | 0.45 | −10.0% | 0.62 | 24.0% |
| 1.0 | 2.57 | 3.08 | 20.0% | 3.73 | 45.0% | 2.83 | 10.0% | 3.74 | 45.0% |
| 1.5 | 6.63 | 7.14 | 7.7% | 8.93 | 34.7% | 7.85 | 18.4% | 9.64 | 45.4% |
| 2.0 | 12.05 | 12.05 | 0% | 15.50 | 28.6% | 14.46 | 20.0% | 16.77 | 39.0% |
| 2.5 | 18.08 | 17.36 | | 22.50 | 24.4% | 21.61 | 19.5% | 24.24 | 34.0% |
| 3.0 | 24.22 | 22.59 | | 29.38 | 21.3% | 28.64 | 18.2% | 31.53 | 30.0% |
| 4.0 | 35.99 | 32.20 | | 41.63 | 15.7% | 41.06 | 14.0% | 44.58 | 23.9% |
| 6.0 | 54.88 | 46.68 | | 59.39 | 8.2% | 58.84 | 7.2% | 63.02 | 14.8% |

Day/Night Activity Data: Day and night activity was evaluated 24 hours before and 48 hours after oral administration of melatonin at 0 (placebo), 0.01, 0.1, 1, and 3 mg/kg BW. The results are shown in Table 7. The activity data is separated into 3 periods within a 24 hour period. Activity monitoring during the late afternoon light phase (2 pm to 5:30 pm) did not demonstrate any influence of oral melatonin on activity. The activity during the afternoon phase increased in all groups on day 2 (immediately after oral dose or placebo). However, dogs in the 0.01, 0.1, and 1 mg/kg groups did demonstrate a decrease compared to the placebo groups during the dark phase immediately following oral ingestion of melatonin. The morning light phase did not demonstrate a difference in activity on day 2, as the placebo and all melatonin groups, with the exception of the 3 mg/kg group, had a decrease in activity compared to day 1. In addition, there was a continued decrease in activity in all groups on day 3 compared to day 2. Therefore, oral administration does not seem to impact activity of dogs in the daylight hours, but when administered in the afternoon, nighttime activity is slightly reduced.

TABLE 7

| | Melatonin Treatment | | | | |
| --- | --- | --- | --- | --- | --- |
| | Placebo | 0.01 | 0.1 | 1 | 3 |
| Afternoon Light Phase | | | | | |
| Day 1 | 27164 | 30064 | 28140 | 34376 | 30548 |
| Day 2 | 29020 | 44935 | 30124 | 44889 | 45730 |
| Day 3 | 23533 | 39386 | 21497 | 31184 | 35034 |
| Dark Phase | | | | | |
| Day 1 | 23251 | 32346 | 38464 | 47178 | 33517 |
| Day 2 | 35364 | 30930 | 30753 | 26733 | 35926 |
| Day 3 | 23238 | 34140 | 32849 | 49958 | 33492 |
| Morning Light Phase | | | | | |
| Day 1 | 110298 | 140160 | 133337 | 155482 | 139265 |
| Day 2 | 101921 | 128216 | 130972 | 151573 | 153805 |
| Day 3 | 96036 | 120706 | 99800 | 126103 | 117374 |

In the specification, there have been disclosed typical preferred embodiments of the invention and, although specific terms are employed, they are used in a generic and descriptive sense only and not for purposes of limitation, the scope of the invention being set forth in the claims. Obviously many modifications and variations of the invention are possible in light of the above teachings. It is therefore to be understood that within the scope of the appended claims the invention may be practiced otherwise than as specifically described.

What is claimed is:

1. A method for enhancing gastrointestinal absorption of peptides, peptidomimetics, and other gastrointestinal transport protein substrates in an animal comprising:
    a) identifying an animal in which the enhancing of gastrointestinal absorption of peptides, peptidomimetics and other gastrointestinal transport protein substrates is desired, wherein the animal has a malabsorptive disorder, and wherein the animal is a companion animal; and
    b) administering into the gastrointestinal tract of the animal an amount of melatonin effective for enhancing the gastrointestinal absorption of the peptides, peptidomimetics, and other gastrointestinal transport protein substrates in the animal.
2. The method of claim 1 comprising administering the melatonin in conjunction with the peptides, peptidomimetics, or substrates.
3. The method of claim 1 comprising administering the melatonin in a food composition.
4. The method of claim 3 wherein the food composition is administered comprising administering the food composition in conjunction with the peptides, peptidomimetics, or substrates.
5. The method of claim 1 comprising administering the melatonin in an amount from about 0.1 mg/kg to about 50 mg/kg.
6. The method of claim 1 comprising administering the melatonin in an amount from about 1 mg/kg to about 5 mg/kg.
7. The method of claim 1 wherein the gastrointestinal absorption of the peptides, peptidomimetics, and other gastrointestinal transport protein substrates occurs at least in part via an intestinal peptide transport protein within the animal's gastrointestinal system, wherein the intestinal peptide transport protein is a member of the PTR2 family of membrane transporters and wherein the administration of the melatonin increases the activity of the intestinal peptide transport protein in the animal as compared with an equivalent animal that has not been administered the melatonin.
8. The method of claim 7 wherein the intestinal peptide transport protein is Peptide Transporter 1 (PepT1).
9. The method of claim 1 wherein the peptide, peptidomimetic, or substrate is a nutrient or drug.
10. The method of claim 9 wherein the drug is an antibiotic.
11. The method of claim 1 comprising administering the melatonin in conjunction with one or more stimulants

* * * * *